US00PP26900P3

(12) United States Plant Patent
Zaiger et al.

(10) Patent No.: US PP26,900 P3
(45) Date of Patent: Jul. 5, 2016

(54) PEACH TREE NAMED 'SNOW GYPSY'

(50) Latin Name: *Prunus persica*
Varietal Denomination: Snow Gypsy

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 78 days.

(21) Appl. No.: 14/544,060

(22) Filed: Nov. 21, 2014

(65) Prior Publication Data

US 2016/0150702 P1 May 26, 2016

(51) Int. Cl.
*A01H 5/08* (2006.01)

(52) U.S. Cl.
USPC ..... Plt./196

(58) Field of Classification Search
USPC ..... Plt./196
See application file for complete search history.

*Primary Examiner* — Anne Grunberg

(57) ABSTRACT

A new and distinct variety of peach tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous, upright tree growth.
2. Heavy and regular production of large size fruit.
3. Firm, white flesh fruit with very good flavor and eating quality.
4. Fruit with attractive red skin color.
5. Fruit with good storage and shipping quality.

1 Drawing Sheet

Botanical designation: *Prunus persica.*
Variety denomination: 'Snow Gypsy'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES

Among the existing varieties of peach trees, which are known to us, and mentioned herein, 'Sweet Dream' Peach (U.S. Plant Pat. No. 10,176), 'September Snow' Peach (U.S. Plant Pat. No. 8,003), our proprietary non-patented peach seedling selections '233LK471', '66EG140', '373LH55' and '246LC568'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. as a first generation cross between two proprietary non-patented peach seedlings with the field identification numbers '233LK471' and '373LH55'. The non-patented peach seed parent '233LK471' originated as an open pollinated seedling from our proprietary peach seedling '66EG140' (non-patented). The non-patented peach pollen parent '373LH55' originated as a first generation seedling from the cross of the proprietary peach seedling '246LC568' (non-patented) and 'Sweet Dream' Peach (U.S. Plant Pat. No. 10,176). A large number of these first generation seedlings were grown on their own root system and under close and careful observation we recognized the desirable fruit and tree characteristics of the present new variety and selected it in 2003 for asexual propagation and commercialization.

ASEXUAL REPRODUCTION OF THE VARIETY

In 2003 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The new variety of peach tree (*Prunus persica*) is of large size, vigorous, upright growth and a productive and regular bearer of large size, firm, white flesh fruit. The fruit is further characterized by having very good flavor and eating quality, with an attractive red skin color, good handling and shipping quality. In comparison to its non-patented peach seed parent '233LK471' the fruit of the new variety ripens approximately 10 days later. In comparison to its non-patented peach pollen parent '373LH55' the flesh of the new variety is white compared to yellow. In comparison to the commercial variety 'September Snow' Peach (U.S. Plant Pat. No. 8,003) the fruit of the new variety ripens approximately 7 days later.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 10 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 10 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2.5 meters in height the first growing season. Varies slightly with type and fertility of soil, climatic conditions and cultural practices.

*Form*.—Upright, usually pruned to vase shape.

*Branching habit*.—Upright, crotch angle approximately 30°, increases with heavy crop load.

*Productivity*.—Productive, normal fruit thinning necessary for desirable market size fruit. Fruit set varies with climatic conditions during blooming period.

*Bearer*.—Regular, adequate fruit set 8 consecutive years.

*Fertility*.—Self-fertile.

*Density*.—Medium dense, pruning to open center of tree to vase shape desirable to enhance fruit color and keep fruit wood healthy.

*Hardiness*.—Hardy in all stone fruit growing areas of California. Tree grown in USDA Hardiness Zone 9. Winter chilling requirement approximately 950 hours at or below 45° F.

Trunk:

*Size*.—Large, circumference 55.9 cm at 25.4 cm above ground.

*Stocky*.—Medium stocky.

*Texture*.—Medium shaggy, roughness increases with age.

*Color*.—Varies from 1YR 3/4 to 2.5Y 4/2.

Branches:

*Size*.—Medium. Average circumference 20.6 cm at 1.2 meters above ground. Crotch angle approximately 30°, increases with heavy crop load.

*Surface texture*.—New growth relatively smooth. Mature growth medium rough, roughness increases with age.

*Lenticels*.—Average number 21 in a 25.8 sq cm section of branch. Average length 5.5 mm. Average width 2.3 mm. Color varies from 7.5YR 6/10 to 10YR 6/10.

*Color*.—New growth varies from 5GY 6/8 to 5R 3/6. Old growth varies from 10YR 3/74 to 2.5Y 3/4, varies with age of growth.

Leaves:

*Size*.—Large. Average length 146.6 mm. Average width 42.7 mm.

*Form*.—Lanceolate.

*Apex*.—Acuminate.

*Base*.—Cuneate.

*Margin*.—Serrate.

*Thickness*.—Medium.

*Surface texture*.—Upper surface relatively smooth, slightly indented over midrib and leaf veins. Lower surface relatively smooth except for small ridges created by midrib and pinnate venation. Both surfaces glabrous.

*Petiole*.—Average length 12.5 mm. Average width 1.7 mm. Surface glabrous. Longitudinally grooved. Color varies from 5GY 6/6 to 5GY 5/6.

*Glands*.—Type — reniform. Size — medium to large. Average length 1.3 mm. Average diameter 1.0 mm. Number varies from 2 to 4, average number 3. Located primarily on the base of the leaf blade and the upper portion of the petiole. Color varies from 5GY 6/6 to 5GY 7/6.

*Stipules*.—Average number — 2. Average length 6.8 mm. Margin — pectinate. Color varies from 5GY 8/6 to 5GY 7/6.

*Color*.—Upper surface varies from 7.5GY 3/4 to 7.5GY 2/4. Lower surface varies from 5GY 4/4 to 7.5GY 4/4. Midvein color varies from 5GY 8/4 to 5GY 7/6.

Flower buds:

*Size*.—Medium to large. Average length 16.9 mm. Average diameter 8.6 mm.

*Hardiness*.—Hardy with respect to California winters.

*Form*.—Plump, conical, becoming elongated before opening.

*Pedicel*.—Average length 4.4 mm. Average width 1.3 mm. Color varies from 2.5GY 6/8 to 5GY 7/10.

*Color*.—Varies from 5RP 8/4 to 5RP 6/2.

*Density*.—Medium dense.

Flowers:

*Blooming period*.—Date of First Bloom Feb. 16, 2014. Date of Petal Fall Feb. 26, 2014, varies slightly with climatic conditions.

*Size*.—Large, showy. Average height 23.5 mm. Average diameter 47.3 mm.

*Petals*.—Normally 5, alternately arranged to the sepals. Size — large. Average length 23.2 mm. Average width 19.3 mm. Form — obovate, narrowing at point of attachment. Petal apex — rounded. Petal base — acuminate. Margin — sinuate. Arrangement — overlapping. Color varies from 2.5RP 7/8 to 5RP 7/6, fades with age of flower. Both surfaces glabrous.

*Sepals*.—Normally 5, alternately arranged to the petals. Average length 5.8 mm. Average width 6.0 mm. Shape — ovate. Apex — rounded to triangular. Margin entire. Upper surface glabrous, lower surface pubescent. Color — upper surface varies from 5GY 5/6 to 5GY 5/8. Lower surface varies from 7.5R 2/6 to 7.5R 3/4.

*Stamens*.—Average number per flower 50. Average filament length 18.0 mm. On average, the stamens are even with the height of the petals. Filament color N 9.5/ (white) to 5RP 4/8 as flower ages. Anther color varies from 5R 3/8 to 2.5Y 8/6.

*Pollen*.—Self-fertile. Color varies from 5Y 8.5/12 to 5Y 8/10.

*Pistil*.—Normally 1. Surface — pubescent. Average length 19.4 mm. Position of stigma approximately 1.0 mm below anthers. Color varies from 2.5GY 7/6 to 10Y 7/8.

*Fragrance*.—Moderate.

*Color*.—Varies from 5RP 8/4 to 5RP 6/12.

*Pedicel*.—Average length 4.7 mm. Average width 1.3 mm. Color varies from 5GY 7/8 to 2.5GY 6/8. Surface glabrous.

*Number flowers per flower bud*.—Normally one.

Fruit:

*Maturity when described*.—Firm ripe and ready to consume.

*Date of first picking*.—Sep. 1, 2014.

*Date of last picking*.—Sep. 8, 2014, varies slightly with climatic conditions.

*Size*.—Large. Average diameter axially 79.6 mm. Average transversely in suture plane 87.7 mm. Average weight 346.5 grams, varies slightly with fertility of the soil, amount of thinning and climatic conditions.

*Form*.—Globose.

*Suture*.—Nearly smooth to very slightly lipped. Extends from base to apex.

*Ventral surface*.—Nearly smooth.

*Apex*.—Slightly retuse.

*Base*.—Flat.

*Stem cavity*.—Rounded to slightly elongated in suture plane. Average depth 6.1 mm. Average diameter 5.1 mm.

Stem:

*Size*.—Small. Average length 11.1 mm. Average diameter 3.5 mm.

*Color*.—Varies from 5GY 6/6 to 5GY 5/8.

Skin:

*Thickness*.—Medium.

*Surface*.—Smooth.

*Pubescence*.—Pubescent, moderate amount, very short.

*Tendency to crack*.—None.

*Color*.—Ground color varies from 5Y 9/4 to 5Y 9/6. Overspread with 5R 3/6 to 7.R 2/4.

*Tenacity*.—Tenacious to flesh.

*Astringency*.—None.

Flesh:

*Ripens*.—Evenly.

*Texture*.—Firm, meaty, crisp.

*Fibers*.—Few, small, tender.

*Firmness*.—Good, comparable to other commercial varieties.

*Aroma*.—Slight.

*Amydgalin*.—Undetected.

*Eating quality*.—Very good.

*Flavor*.—Very good, sweet, mild, sub-acid flavor.

*Juice*.—Moderate amount, enhances flavor.

*Acidity*.—Not available.

*Brix*.—Average Brix of 12.0°, varies slightly with amount of fruit per tree and climatic conditions.

*Color*.—Varies from 5Y 9/2 to 7.5Y 9/2.

*Pit cavity*.—Average length 40.0 mm. Average width 24.7 mm. Average depth 10.0 mm. Color varies from 5R 3/8 to 7.5R 3/10.

Stone:

*Type*.—Freestone. Adherence to flesh not present, weak.

*Size*.—Large. Average length 38.9 mm. Average width 22.9 mm. Average thickness 16.1 mm.

*Form*.—Ovoid.

*Base*.—Flat.

*Apex*.—Pointed. Average length 2.9 mm.

*Surface*.—Pitted throughout, pits vary from rounded to slightly elongated.

*Sides*.—Unequal, with one side extending further from the suture plane.

*Ridges*.—Numerous, extending from base to apex.

*Tendency to split*.—None.

*Color*.—Varies from 10R 2/4 to 2.5YR 2/4 when dry.

Kernel:

*Size*.—Large. Average length 20.2 mm. Average width 10.4 mm. Average depth 5.4 mm.

*Form*.—Ovoid.

*Viability*.—Viable, complete embryo development.

*Skin color*.—Varies from 5Y 9/4 to 5Y 8.5/6.

Use: Dessert.

*Market*.—Local and long distance.

Keeping quality: Good, held firm in cold storage at 38° to 42° F. for 3 weeks without internal breakdown of flesh or appreciable loss of flavor.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree, substantially as illustrated and described.

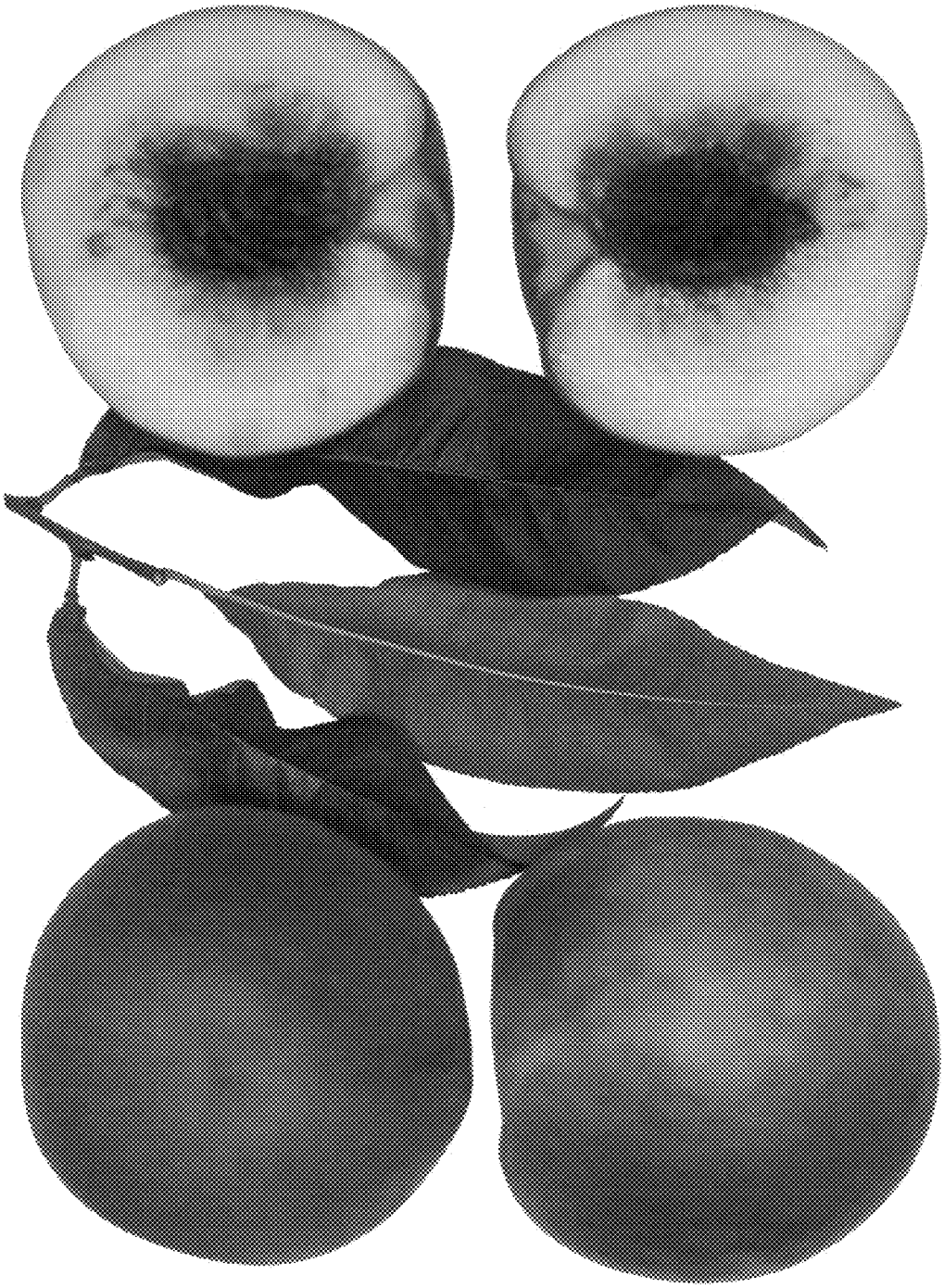

* * * * *